United States Patent [19]

Lindstrom

[11] Patent Number: 4,619,656
[45] Date of Patent: Oct. 28, 1986

[54] INTRAOCULAR LENS

[76] Inventor: Richard L. Lindstrom, 1065 W. Ferndale Rd., Wayzata, Minn. 55391

[21] Appl. No.: 569,610

[22] Filed: Jan. 10, 1984

[51] Int. Cl.⁴ ............................................. A61F 2/16
[52] U.S. Cl. ..................................... 623/6; 128/303 R
[58] Field of Search .............. 3/13; 128/303 R; 623/6

[56] References Cited

U.S. PATENT DOCUMENTS

| 4,190,049 | 2/1980 | Hager et al. | 3/13 X |
| 4,298,995 | 11/1981 | Poler | 3/13 |
| 4,326,306 | 4/1982 | Poler | 3/13 |
| 4,418,431 | 12/1983 | Feaster | 3/13 |

OTHER PUBLICATIONS

Anterior Chamber and/or Posterior Chamber Model, 120 Feaster Dualens (Advertisement Sheet), Coburn Professional Products Div., P.O. Box 2498, Clearwater, Fla. 33517 (1 page) Aug. 1983, 623-6.

Primary Examiner—Ronald L. Frinks
Attorney, Agent, or Firm—Hugh D. Jaeger

[57] ABSTRACT

Intraocular lens implant including an optic such as a plano-convex lens, a plurality of outwardly extending loops, and at least one key-hole affixed to one of the loops. In one embodiment, a plano-convex posterior-chamber lens implant is provided with at least one key-hole loop in one of the two loops for turn-key insertion by locking a turn-key insertion instrument into a key-hole where the key-hole is at one end of one or both of the loops. The key locking into the key-hole provides for turn-key insertion of the loop with stable, secure, fixation, and control of the superior loop providing movement in all directions and all planes. This provides for rotation of the loop to rotate the lens implant posterior to the iris or into the capsular bag during a superior loop insertion technique.

10 Claims, 17 Drawing Figures

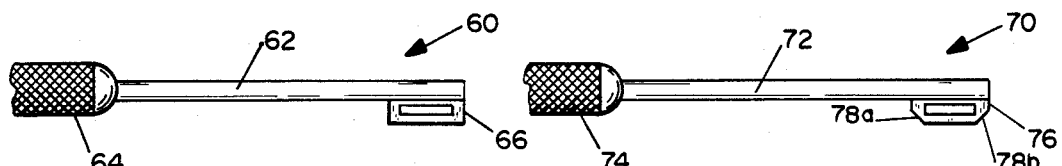
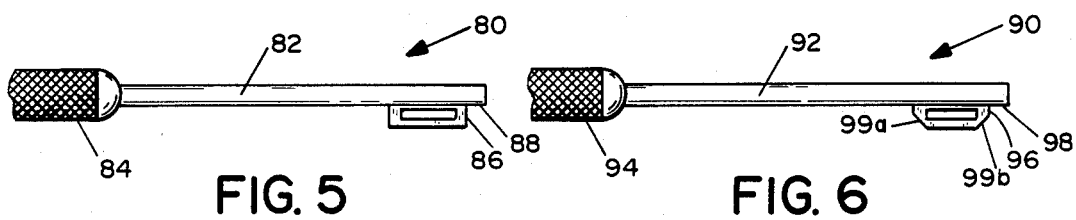
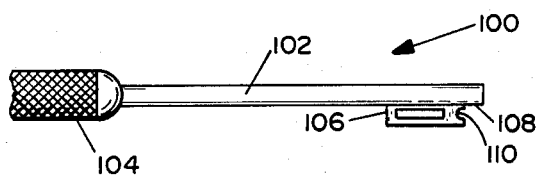
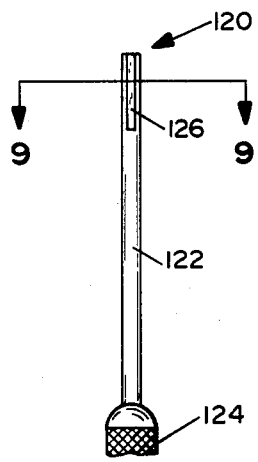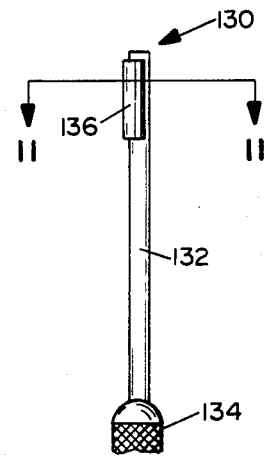
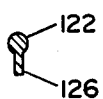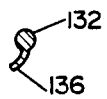

INTRAOCULAR LENS

BACKGROUND OF THE INVENTION

1. Field of the Invention

The present invention pertains to an intraocular lens implantable during surgery, and more particularly, pertains to an intraocular lens with a key-hole in one of the loops of the lens.

2. Description of the Prior Art

Prior art lenses have utilized lenses with an insertion hole in one of the loops. One particular example is a posterior chamber lens with a circular hole in one of the loops and including a round peg extending outwardly perpendicular from a longitudinal member. The round peg is inserted into the round hole in the end of the posterior chamber loop, but this provides little control as the round peg rotates within the round loop and also is able to slide off of the round peg.

Other individuals have referred to this type of hole in the end of the loop as an eyelet, which is engaged by hook, but the hook can sometimes engage portions of the eye or related anatomical membranes which causes damage.

The present invention overcomes the disadvantages of the prior art by providing a lens with a key-hole loop for turn-key instrument insertion and locking of the key into the key-hole of the loop during insertion.

SUMMARY OF THE INVENTION

A general purpose of the present invention is a turn-key insertion process for use with an intraocular lens including a key-hole loop where a key is locked into the key-hole.

According to one embodiment of the present invention, there is provided an intraocular lens with a key-hole loop providing for insertion and locking of a turn-key insertion instrument into the key-hole thereby providing for turn-key insertion. Specifically, a plano-convex lens can be provided with at least one key-hole of a predetermined geometrical configuration in a loop. More specifically, a plano-convex lens having two open loops such as that in a posterior chamber lens can include a key-hole which is a geometricalpredetermined configuration such as a rectangular configuration and this example, by way of illustration and for purposes of example only and not to be construed as limiting in the present invention, where a corresponding turn-key insertion instrument with a geometrical like configuration is frictionally engaged into the key-hole for subsequent rotation and insertion of the lens during superior loop insertion. The principles of the present invention are applicable, not only to a posterior chamber lens, but also to an anterior chamber lens intraocular lens implants.

One significant aspect and feature of the present invention is a key-hole which can be applied to a loop or more than one loops and can take any geometrical configuration with respect to a corresponding key. The turn-key insertion instrument can be either a straight key or curved key on a shank, and can take any geometrical configuration whether it be rectangular, include a curve or curves, or be any other geometrical design.

Another significant aspect and feature of the present invention is a key-hole providing for turn-key instrument insertion which is particularly applicable to posterior chamber lenses.

A further significant aspect and feature of the present invention is a process providing for rotation of the loop end for rotating the elbow of the lens implant loop posterior during superior loop insertion technique.

Having thus described the embodiments of the present invention, it is the principle object hereof to provide a turn-key insertion process for locking a key into a key-hole of a loop of an intraocular lens for subsequent insertion into the eye.

Objects of the present invention include providing different types of turn-key insertion instruments for engagement with corresponding geometrical key-holes in loops of intraocular lenses.

Other objects of the present invention provide for insertion techniques for loops of intraocular lenses including the specific key-hole loops and corresponding turn-keys for the insertion of the loops into either posterior or anterior chambers of the eye.

BRIEF DESCRIPTION OF THE DRAWINGS

FIG. 3 illustrates a rectangular turn-key insertion instrument for the key-hole loop;

FIG. 4 illustrates a rectangular key with tapered edges for the key-hole loop;

FIG. 5 illustrates an offset rectangular key for the key-hole loop;

FIG. 6 illustrates an offset rectangular key with tapered edges for the key-hole loop;

FIG. 7 illustrates a key with an offset and indentation;

FIG. 8 illustrates a plane view of a straight key;

FIG. 9 illustrates an end view taken along line 9—9 of FIG. 8 of straight key;

FIG. 10 illustrates a top view of a curved key;

FIG. 11 illustrates an end view taken along line 11—11 of FIG. 10 of a curved key;

FIG. 12 illustrates placing the key in the key hole;

FIG. 13 illustrates a compression of the superior loop of the key;

FIG. 14 illustrates pushing of the loop;

FIG. 15 illustrates rotating the loop back to the plane behind the iris for insertion in the eye;

DESCRIPTION OF THE PREFERRED EMBODIMENTS

Figure 1:
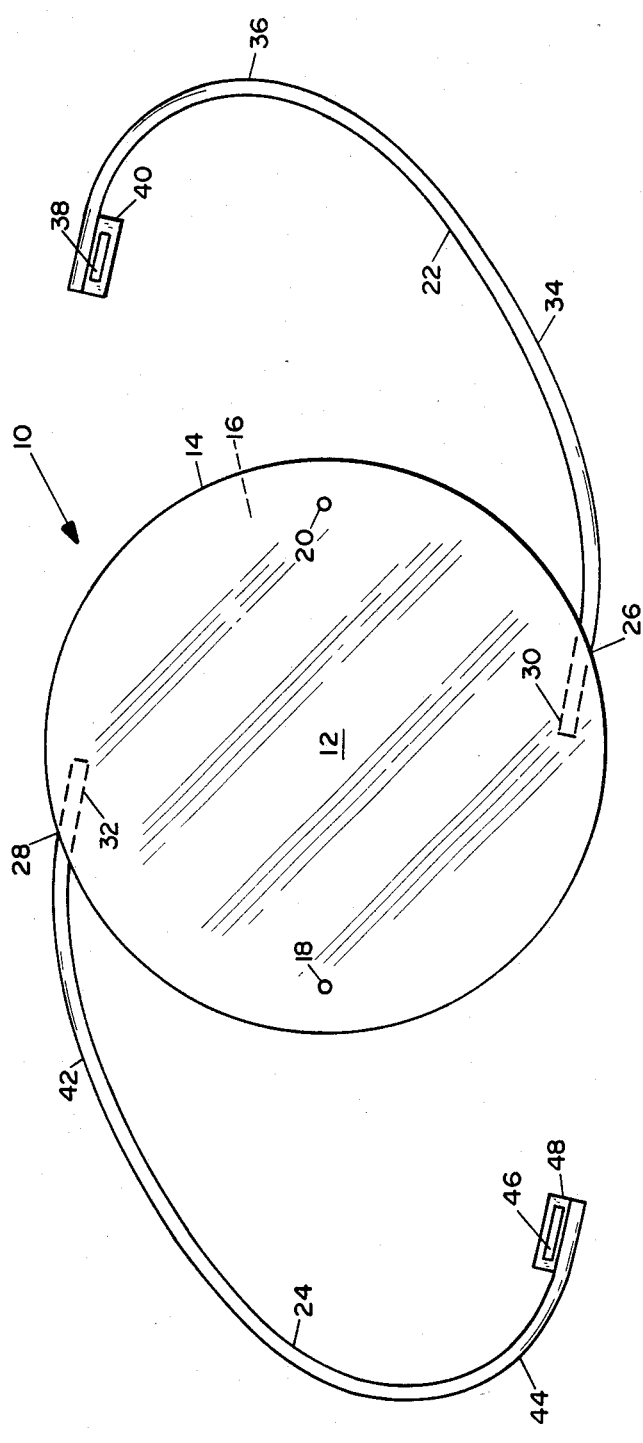
FIG. 1 illustrates a plane view of a intraocular lens including a key-hole loop.

FIG. 1 illustrates a plane view of an intraocular lens 10 with at least one key-hole loop and in this particular embodiment two key-hole loops, of the present invention.

The intraocular lens 10 includes a convex surface 12, a finite edge 14, and a plano surface 16. A plurality of positioning holes 18 and 20 can be provided in the lens and two such holes have been illustrated in this example. Two posterior loops 22 and 24 are anchored and secured through the edge of the lens at points 26 and 28 respectively and secured in holes 30 and 32 respectively. The posterior loop 22 starts off with a large radius of curvature 34 decreasing to a smaller radius of curvature 36 and includes a key-hole 38 at the end of the loop. In this paticular example, and not to be construed as limiting of the invention, the key-hole is rectangular in configuration and is surrounded by a rectangular body 40. The key-hole, as well as the rectangular body can take any geometrical shape and is not limited to the rectangular key-hole configuration nor the rectagnular body configuration. The loop 24 is illustrated with a like radius of curvature 42 and 44 and including a like key-hole 46 surrounded by a body 48. In the alternative, the key-hole and supporting body can be eliminated and the posterior loop 24 could be terminated by a rounded end, a slightly rounded ball or other like ending configurations as noted in the art.

Figure 2:
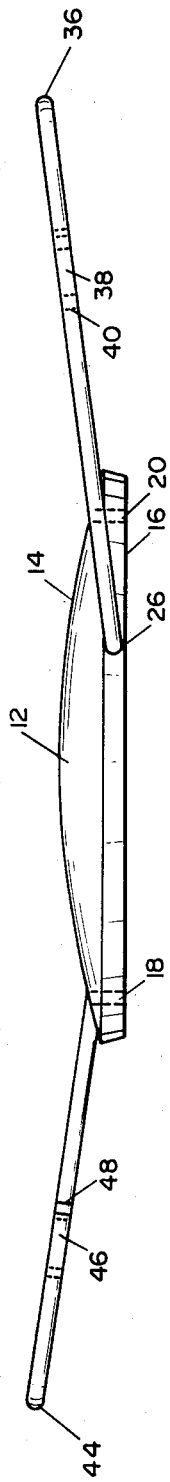
FIG. 2 illustrats a side view of the lens of FIG. 1.

FIG. 2 illustrates a side view of the lens of FIG. 1 where all numerals correspond to those elements previously described. The key-holes in the key-hole bodies at the end of the loop provide no additional weight or significant structural size to the ends of the posterior loops. This is illustrated by the side view of the lens.

FIGS. 3–11 illustrate different geometrical configurations for suitable keys of the present invention.

FIG. 3 illustrates a rectagnular turn-key insertion instrument 60 including a shank 62, a knurled handle 64 at the outer end of the shank 62, and a rectangular key 66 for subsequent engagement with the rectangular key-hole 38.

FIG. 4 illustrates a rectangular key 70 including a shank 72, a knurled handle 74, a rectangular key 76, and tapered edges 78a and 78b.

FIG. 5 illustrates an offset rectangular key 80 including the shaft 82, the knurled handle 84, the rectangular key 86 having the offset 88.

FIG. 6 illustrates an offset rectangular key with tapered edges 90 including a shank 92, a knurled end 94, a configured key 96, an offset 98, and tapered edges 99a and 99b.

FIG. 7 illustrates a key with an offset and indentation 100 including a shaft 102, a knurled handle 104, a rectangular body 106, an offset 108, and a indentation 110.

All of the keys of FIG. 3–FIG. 7 are designed to slightly frictionally engage with the key-hole so as to prevent any movement between the key and key-hole providing for total control of the lens. More so, the key of FIG. 7 provides for interlocking engagement between the key and the key-hole providing for secure and firm control of the loop with respect to the key.

FIG. 8 illustrates an embodiment 120 of a key including a shaft 122, a knurled handle 124, and a key 126. The key is longitudinal and rectangular and aligns with respect to the shaft.

FIG. 10 illustrates a key 130 including a shaft 132 and a knurled handle 134, and also a curved key 136. The keys of FIGS. 3–7 can assume this curved configuration, which provides for slight frictional engagement in the key-hole respectfully.

FIG. 11 is a end view of FIG. 10 where all numerals correspond to those elements previously described.

MODE OF OPERATION

Figure 13:
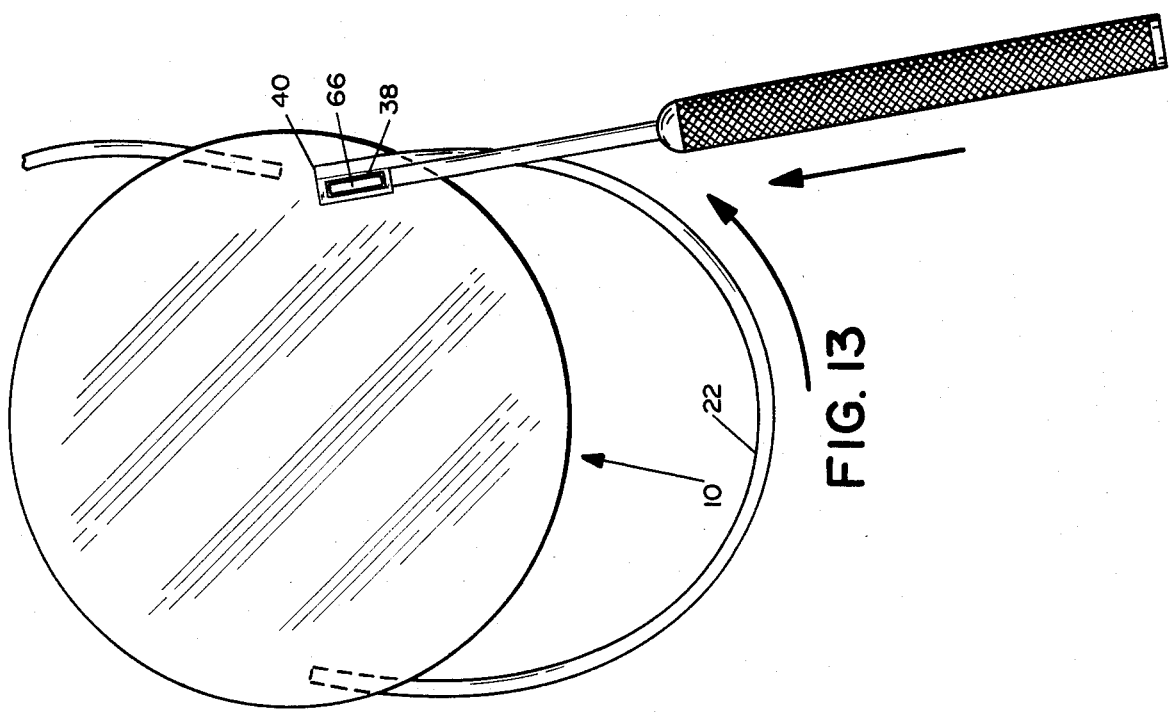
FIGS. 12-15 illustrate views of a process for insertion of an intraocular lens with a key-hole loop with the turn-key insertion instrument including.
Figure 12:
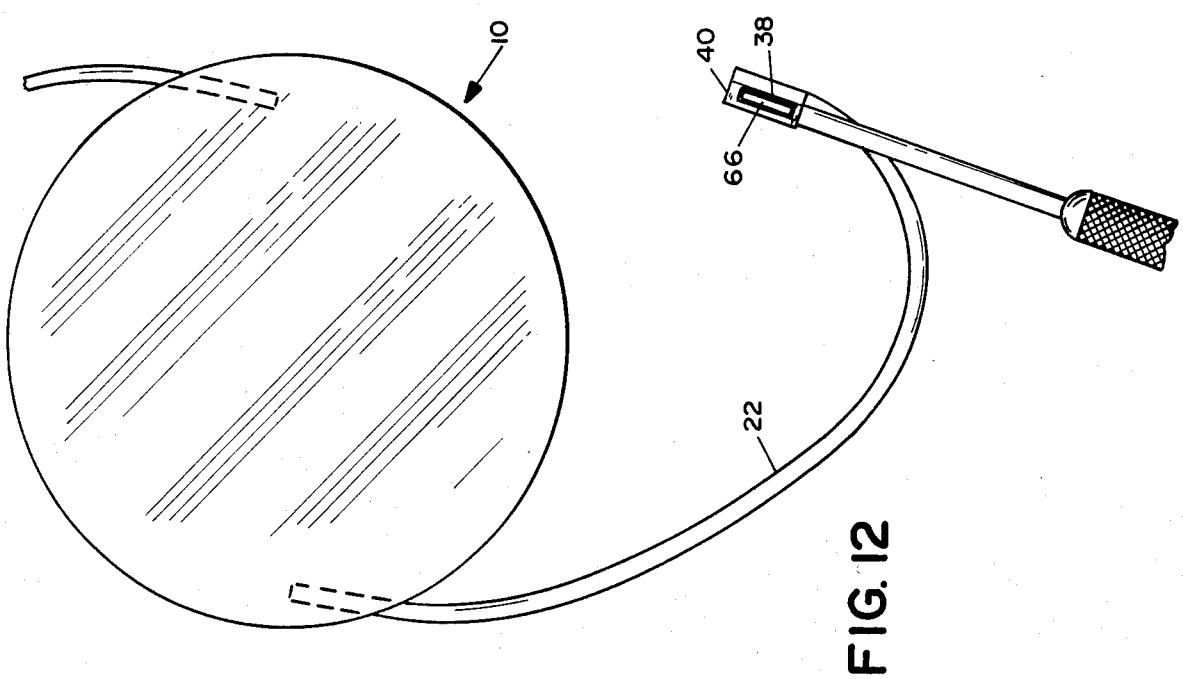
Figure 15:
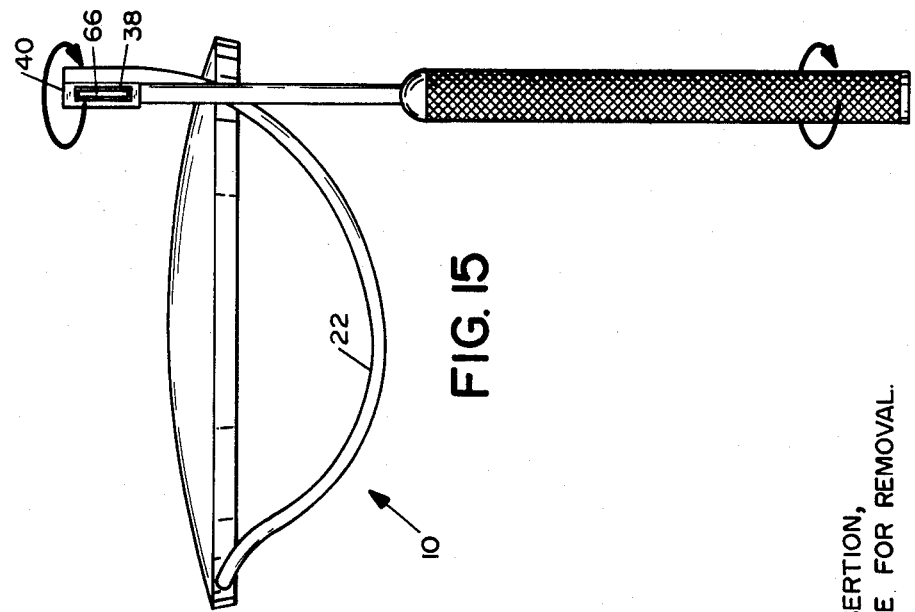
Figure 14:
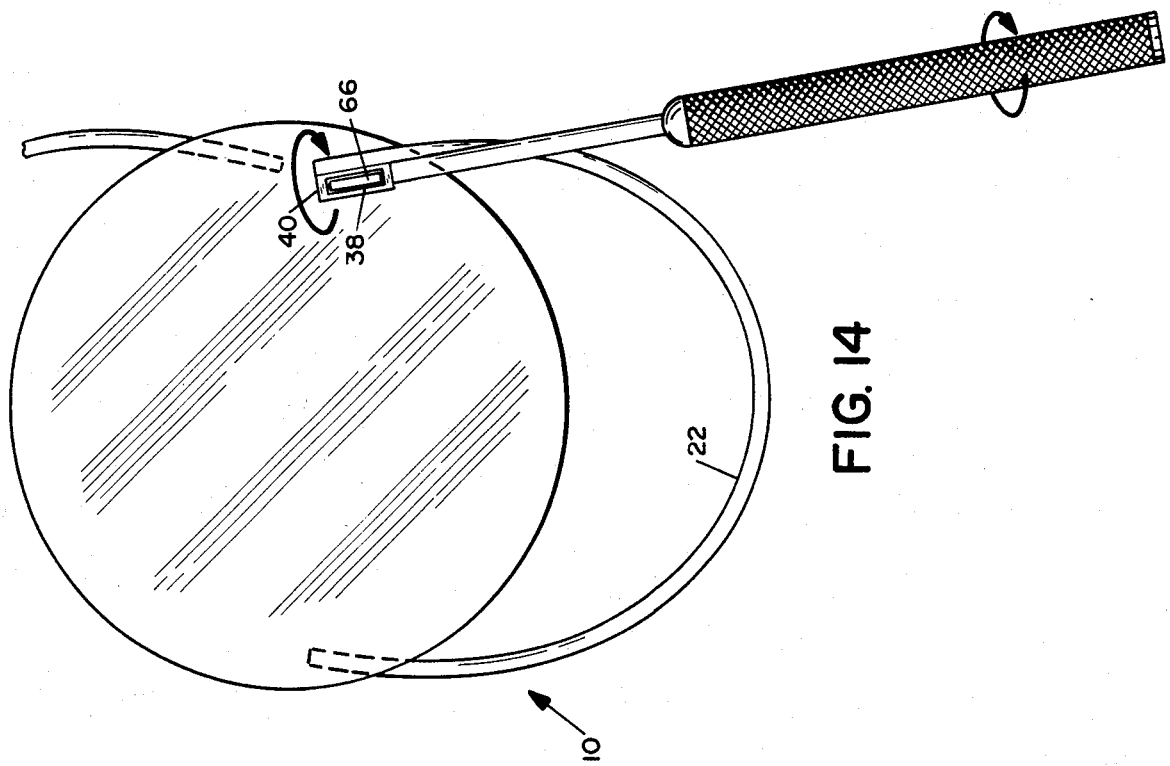

FIGS. 12–15 illustrates views of a process for insertion of an intraocular lens with a key-hole loops with a turn-key insertion instrument. The Lindstrom key-hole lens utilizes a Lindstrom turn-key insertion instrument for inserting the lens into the eye. FIG. 12 illustrates where the key, and in this instance references made to the key of FIG. 3, is inserted into the key-hole 38 of the loops 22. FIG. 13 illustrates where the loop is elbowed by movement from the turn-key insertion instrument 60 providing for movement of the superior loop 22 through motion transferred by the key 66. One of the inventive points of the present invention is that the key is engaged into the key-hole providing for control of the loop which is transferred to the lens opposed to the prior art, where the prior art hooks and eyelets would allow the loop, as well as the lens to rotate freely. FIG. 14 illustrates where the key shank carrying the key is turned to the left that is counter clockwise, rotating the loop back to the plane behind the iris of the lens. FIG. 15 illustrates this final insertion showing the elbow of the loop being rotated back to the plane behind the iris.

Another process of insertion provides that the whole lens can be depressed towards the posterior chamber while turning the key providing for total control of the lens, as well as the inferior and posterior loops. The turn-key process allows for side-to-side motion of the intraocular lens under full control.

All that is necessary to release the turn-key insertion instrument from the key-hole is to turn the turn-key instrument clockwise in a reverse direction of the rotation arrow of FIGS. 14 and 15, and gently slide the key on the turn-key insertion instrument from the eye. Likewise, the same movement is required for removing the lens from the eye. While inserting the intraocular lens, there is a certain pressure in addition to the slight frictional engagement of the key with respect to the key-hole, but once the lens and loops are positioned, the pressure between the key and key-hole can be relaxed providing for easy disengagement between the key and the key-hole.

Figure 16:
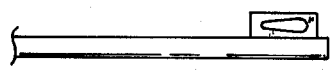
FIG. 16 illustrates a section of loop with an oval configuration.
Figure 17:
FIG. 17 illustrates a section of loop with a square configuration.

The geometrical configuration of the key-hole at the end of the loop can assume any geometrical configruation and is not limited to a rectangular configuration as illustrated. The configuration can also include a oval configuration as illustrated in FIG. 16, a square configuration as illustrated in FIG. 17, a curved configuration, or any other like geometrical configuration other than a circular configuration. Accordingly, the key would correspond to the geometrical configuration. Also, the key-hole can be positioned in anterior chamber lenses, as well as posterior chamber lenses, for insertion of anterior chamber lenses.

The key-hole of the present invention could be placed at a junction of a loop end optic or in the alternative in a portion of the optic depending of course on the diameter of the optic. The key-hole has only been illustrated at the end of a loop by way of example and for urposees of illustration, and is not be construed as limiting of the present invention.

The Key-hole can also accommodate different geometrically shaped keys for which different surgeons may have a preference for an individual geometrically shaped key such as a straight rectangular or a curved rectangular key.

I claim:

1. In combination, intraocular lens with a key-hole loop and a turn-key insertion instrument comprising:
   a. intraocular lens including a lens optic at least one loop outwardly from said lens optic, and at least one non-circular key hole positioned in at least one of said loops; and
   b. turn-key insertion instrument including a key having a corresponding geometrical relationship to said key-hole providing for key insertion of the intraocular lens into the eye.

2. Combination of claim 1 wherein said key-hole is rectangular.

3. Combination of claim 1 wherein said key is rectangular.

4. Combination of claim 1 wherein said key is offset on a shank.

5. Combination of claim 1 wherein said key includes an offset indentation with respect to a shank.

6. Combination of claim 1 wherein said key is straight.

7. Combination of claim 1 wherein said key is curved with respect to a shank.

8. Process of turn-key insertion of an intraocular lens comprising the step of:
   a. positioning an intraocular lens with loops including at least one non-circular key-hole in one of the loops;
   b. placing a turn-key insertion instrument including a key into slight frictional engagement within said key-hole;
   c. looping one of said loops of the intraocular lens in compressing the superior loop with the key;
   d. turning the key to the left; and
   e. rotating the turn-key insertion instrument counter clockwise for rotating said one loop back to the plane behind the iris into the capsular bag for positioning of the lens in the eye.

9. Process of claim 8 comprising the step of rotating said turn-key insertion instrument providing for removal of said lens from the eye.

10. Process of claim 8 wherein said lens is a posterior chamber lens.

* * * * *